US008851281B2

(12) United States Patent
Leabeater et al.

(10) Patent No.: US 8,851,281 B2
(45) Date of Patent: Oct. 7, 2014

(54) SHARPS CONTAINER

(75) Inventors: Michael Patrick Leabeater, Kurmond (AU); Peter Mandavy, Prestons (AU)

(73) Assignee: ASP Rights Management Pty Ltd, Sydney, NSW (AU)

( * ) Notice: Subject to any disclaimer, the term of this patent is extended or adjusted under 35 U.S.C. 154(b) by 0 days.

(21) Appl. No.: 12/911,826

(22) Filed: Oct. 26, 2010

(65) Prior Publication Data

US 2011/0094909 A1     Apr. 28, 2011

(30) Foreign Application Priority Data

Oct. 26, 2009 (AU) ................................ 2009905205

(51) Int. Cl.
*A61B 19/02* (2006.01)
*B65D 81/00* (2006.01)

(52) U.S. Cl.
USPC ...................... 206/364; 220/560.01; 220/666

(58) Field of Classification Search
USPC .......... 206/365, 366, 306; 604/192, 363, 110; 220/666, 667
See application file for complete search history.

(56) References Cited

U.S. PATENT DOCUMENTS

| | | | | | |
|---|---|---|---|---|---|
| 3,342,319 | A | * | 9/1967 | Faulseit | 206/365 |
| 3,473,524 | A | * | 10/1969 | Drewe | 604/216 |
| 3,712,295 | A | * | 1/1973 | Kline | 604/216 |
| 3,712,302 | A | * | 1/1973 | Burke et al. | 604/110 |
| 4,822,332 | A | * | 4/1989 | Kajander | 604/16 |
| 4,981,476 | A | * | 1/1991 | Aichlmayr et al. | 206/365 |
| 5,015,240 | A | * | 5/1991 | Soproni et al. | 604/192 |
| 5,139,489 | A | * | 8/1992 | Hollister | 604/192 |
| 6,793,882 | B1 | * | 9/2004 | Verschuur | 206/361 |
| 7,392,903 | B2 | * | 7/2008 | Jolley et al. | 206/366 |
| 7,775,357 | B2 | * | 8/2010 | Clarke | 206/365 |

* cited by examiner

*Primary Examiner* — Andrew Perreault
(74) *Attorney, Agent, or Firm* — Design IP

(57) ABSTRACT

A sharps container 10, 20 for used syringes is disclosed which can withstand a crushing force in the direction of the longitudinal axis of a syringe 15 without the needle 11 of the syringe penetrating the base 7 of the container. Instead the container has a portion 120, 22A of reduced wall thickness which concertinas (or zig zags) when such a crushing force is applied.

9 Claims, 4 Drawing Sheets

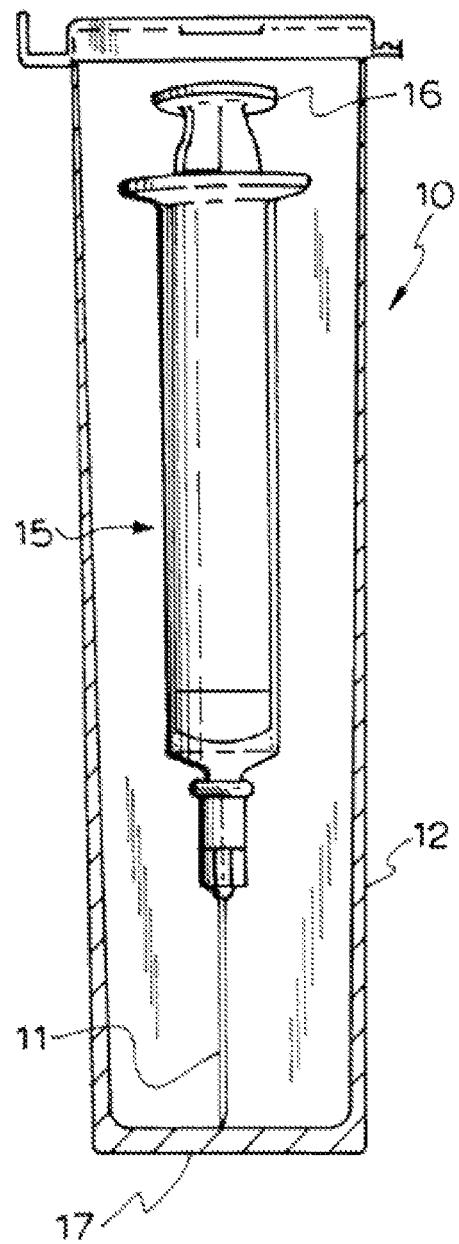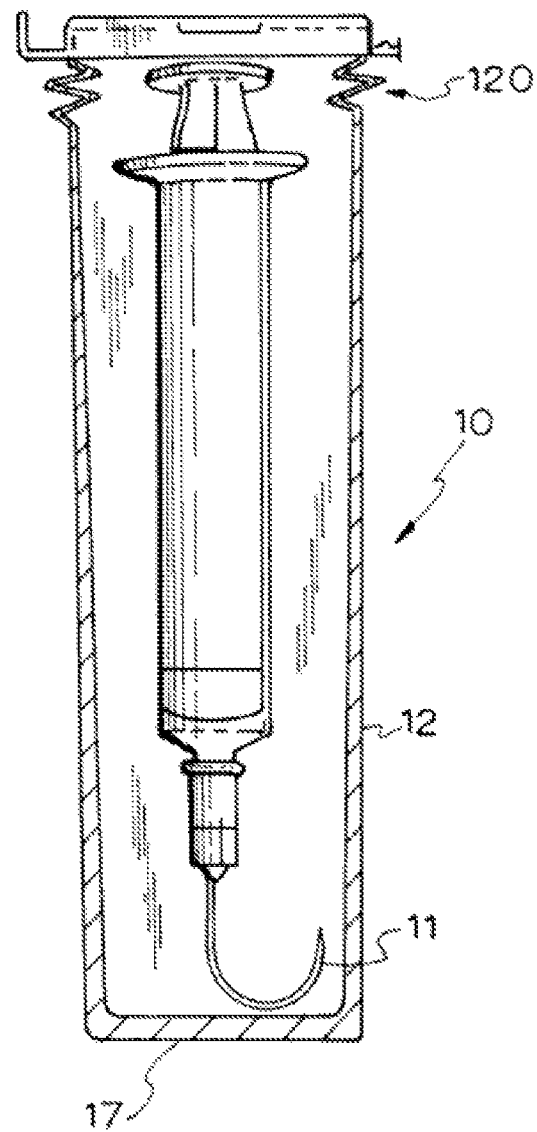

SHARPS CONTAINER

FIELD OF THE INVENTION

The present invention relates to "sharps" containers intended to store used syringes and formed by injection moulding of plastics material such as polypropylene, and the like.

BACKGROUND OF THE INVENTION

Sharps containers are intended for the disposal of syringes which have extremely sharp needle points. Examples of such containers are those illustrated in Australian Patent No. 741, 793 and in the first four drawings of the present specification. Such containers may or may not have an interior partition which divides the container into two, namely one compartment containing unused syringes and the other compartment containing used syringes.

Outside of the hospital and medical systems, there are two types of persons who regularly use syringes for the self-administration of drugs. These are essentially diabetics and intravenous drug addicts. Diabetics are insulin-dependent and require a regular injection of insulin in order to maintain their blood sugar levels. Intravenous drug addicts are dependent upon a drug such as heroin and regularly inject themselves in order to maintain a sense of euphoria.

Both classes of persons carry syringes about them from place to place and thus require a portable means of safe disposal of the syringes after the injection has taken place. For diabetics this is relatively straight forward since the syringes are not in themselves normally infected and thus it is a matter of preventing the needle tip from puncturing anything or anybody.

However, for intravenous drug users, there is a high likelihood that the syringe is infected with either Hepatitis C or HIV AIDS, or both, and thus members of the general public should be protected from the possibility of needle stick injury which may result in permanent and even fatal infection.

It is therefore highly desirable from a public health point of view that intravenous drug users not leave infected syringes lying about in public places such as parks, beaches, and the like where they can be accidentally stepped upon by members of the general public. Thus it is desirable from a public health point of view that intravenous drug users, as well is diabetics, be able to safely dispose of syringes after they have been used. Thus there is a need for an inexpensive portable used syringe container device.

Furthermore, modern and more enlightened public health policy is to prevent, as much as possible, intravenous drug users from sharing needles since this can prevent the spread of Hepatitis C and HIV AIDS. It is therefore desirable that used syringe container devices have a one-way locking arrangement which prevents used syringes once they are inserted in the container, from then being extracted from the container for re-use.

In addition, many intravenous drug users are eventually able to resist and overcome their addiction. Thus if they can be maintained healthy by not contracting Hepatitis C or HIV AIDS whilst they are addicted, this can greatly assist their eventual recovery.

Another aspect of public health is the need to protect the health of sanitary workers such as garbage collectors who may accidentally, or who may routinely be required to, come into contact with such used syringe container devices. Another situation where such containers may be crushed is when seat belt wearing motorists carry such containers in a breast pocket and under a seat belt prior to a motor vehicle accident.

Thus there is a desirable public health outcome if such used syringe containers are able to withstand moderate force and thus can retain the point of the needle within the container. In this way, the incidence of needle stick injuries, even of gloved hands, can be lessened.

GENESIS OF THE INVENTION

The genesis of the present invention is the desire to improve the performance of sharps containers, in particular, when crushed by a seat belt or by garbage handling apparatus.

SUMMARY OF THE INVENTION

In accordance with a first aspect of the present invention there is disclosed a crush survival sharps container having a base, at least one side wall, a top, and a used syringe receiving aperture in said top wherein the or each said side wall has a wall thickness which is greatest adjacent said base and thinnest adjacent said top, wherein said side wall(s) adjacent said top concertina when said container is subjected to a top to base compressive crushing force, and wherein said base and side wall(s) adjacent said base are sufficiently thick to prevent penetration thereof by a needle tip of a used syringe stored needle tip adjacent said base in said container and inserted needle first through said aperture.

In accordance with a second aspect of the present invention there is disclosed a method of providing a crush survival sharps container having a base, at least one side wall, a top, and a used syringe receiving aperture in said top, said method comprising:

providing the or each said side wall with a wall thickness which is greatest adjacent said base and thinnest adjacent said top, and providing said base, and the or each said side wall adjacent said base, sufficiently thick to prevent penetration thereof by a substantially vertically aligned needle, whereby when said container is subjected to a top to base compressive crushing force the side wall(s) adjacent said top concertina, and said base and lower side walls are not penetrated by a needle tip of a syringe stored needle tip adjacent said base in said container.

BRIEF DESCRIPTION OF THE DRAWINGS

Two embodiments of the present invention will now be described, with reference to the accompanying drawings in which:

FIG. 6 is a schematic cross-sectional view of a sharps container having the side wall illustrated in FIG. 5 and showing a used syringe located within the container;

FIG. 7 is a view similar to FIG. 6 but showing the container after undergoing "vertical" crushing.

DETAILED DESCRIPTION OF THE PREFERRED EMBODIMENTS

Figure 1:
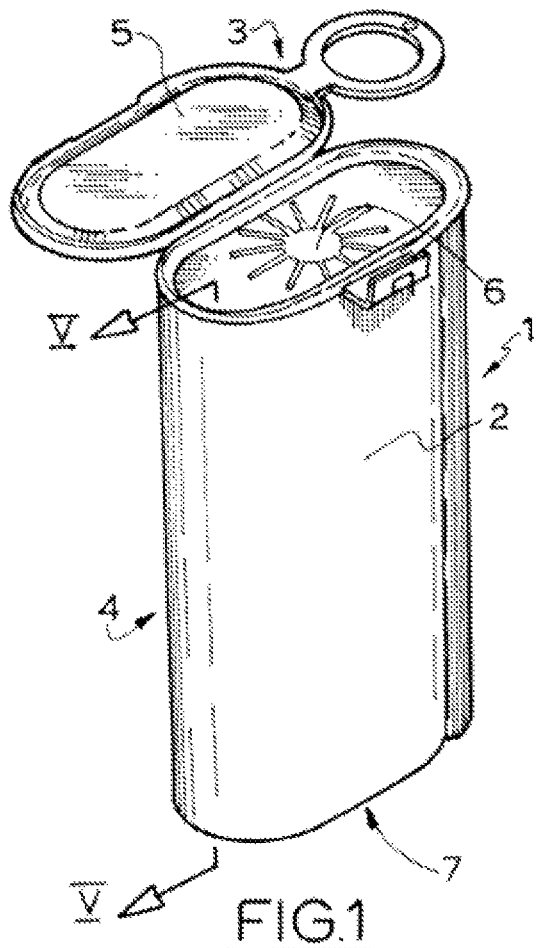
FIG. 1 is a front perspective view from above, with the lid open, of a prior art sharps container.

The ensuing detailed description provides preferred exemplary embodiments only, and is not intended to limit the scope, applicability, or configuration of the invention. Rather, the ensuing detailed description of the preferred exemplary embodiments will provide those skilled in the art with an enabling description for implementing the preferred exemplary embodiments of the invention. It being understood that various changes may be made in the function and arrangement of elements without departing from the spirit and scope of the invention, as set forth in the appended claims.

To aid in describing the invention, directional terms are used in the specification and claims to describe portions of the present invention (e.g., upper, lower, left, right, etc.). These directional definitions are merely intended to assist in describing and claiming the invention and are not intended to limit the invention in any way. In addition, reference numerals that are introduced in the specification in association with a drawing figure may be repeated in one or more subsequent figures without additional description in the specification in order to provide context for other features.

As seen in FIGS. 1 to 4, a prior art sharps container 1 has a top 3 and a container body 4 with a side wall 2 of substantially uniform thickness. The container body 4 and top 3 are each independently injection moulded and are subsequently brought together and joined, for example, by means of ultrasonic welding. The top 3 has a hinged lid 5 and a one way syringe orifice 6 which enables the disposal of used syringes in a substantially safe manner. Not illustrated in FIGS. 1 to 4 but interconnecting the side walls 2 is a base 7 for the container body 4. The container 1 may be considered to have four side walls 2 whilst a cylindrical container may be considered to have a single side wall.

Figure 5:
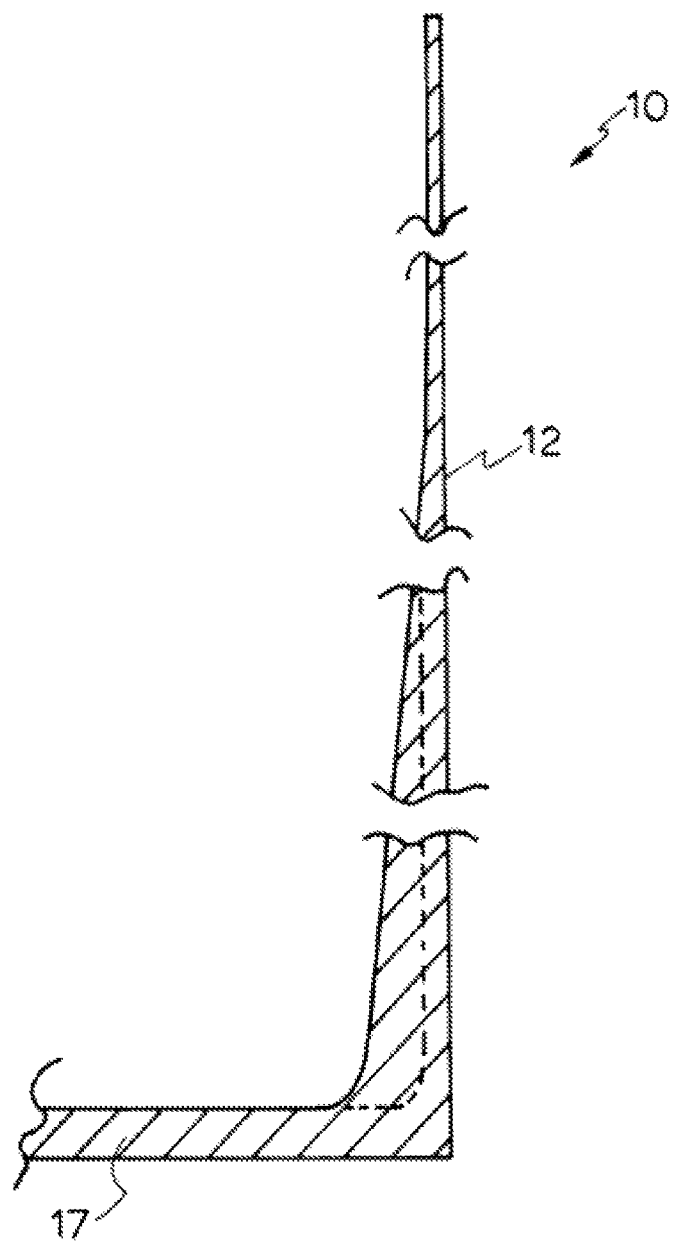
FIG. 5 is a longitudinal cross-sectional view taken along the line V-V of FIG. 1 but in respect of the sharps container of a first embodiment.

Turning now to FIG. 5, a sharps container 10 of a first embodiment has a non-uniform side wall 12 and a base 17. The top portion of the side wall 12 is relatively thin being typically 1.5 mm (0.059 inch) in thickness adjacent the top, but tapers continuously from the top towards the base 17 so as to have a thickness of approximately 2.0 mm (0.079 inch) adjacent the base 17.

Such a container 10 is illustrated schematically in FIG. 6 and is seen to contain a syringe 15 having a plunger 16 and a needle 11. The container of FIG. 6 can be either cylindrical and thus of circular cross-sectional shape, or of generally rectangular cross-sectional shape as illustrated in FIGS. 1 to 4. The syringe 15 is able to be inserted into the container 10 by means of a one way syringe orifice (not illustrated in FIG. 6 but of the type illustrated in FIG. 3).

Figure 2:
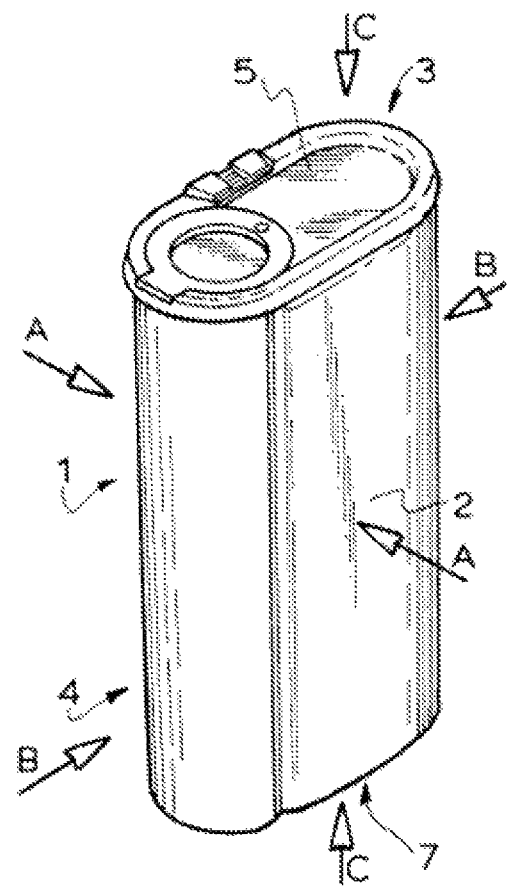
FIG. 2 is a rear perspective view from above, with the lid closed, of the prior art sharps container of FIG. 1.
Figure 3:
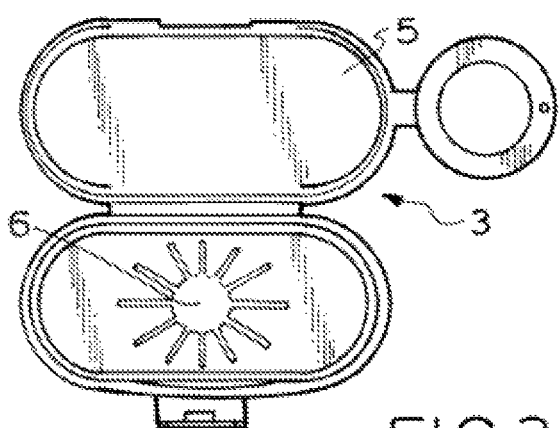
FIG. 3 is a plan view with the lid open of the prior art sharps container of FIGS. 1 and 2.
Figure 4:
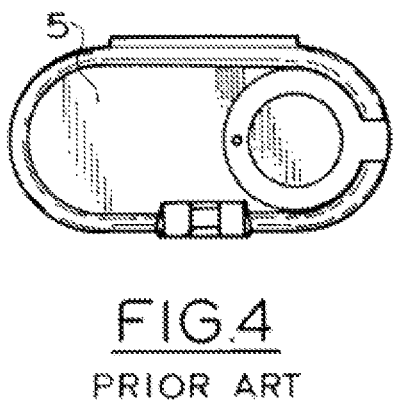
FIG. 4 is a plan view with the lid closed on the prior art sharps container of FIGS. 1 to 3.

As illustrated in FIG. 2, there are three different directions in which a sharps container can be crushed. As indicated by arrows A, one lateral crushing direction is substantially perpendicular to the larger faces of the side wall 2. As indicated by arrows B another lateral crushing direction is substantially perpendicular to the smaller faces of the side wall 2. The prior art container 1 of FIGS. 1 to 4 has no difficulty in adequately passing crushing standards when the crushing forces are applied in the lateral directions indicated by arrows A and B. However, when the prior art container 1 is crushed vertically as indicated by the pair of arrows C, then the prior art container 1 fails the crushing test because needles or syringes contained within the container 1 extend through the container 1 and thus constitute a health hazard.

However, as indicated in FIG. 7, the container 10 because of the tapered side wall 12, when subjected to the crushing forces in the vertical direction indicated by arrows C in FIG. 2, results in the upper portion of the side wall 12 deforming into a zig-zag or concertina pattern 120 as schematically illustrated in FIG. 7. During this vertical crushing operation, not only is the length of the side wall 12 shortened but the energy absorbed by creating the concertina 120 means that the syringe 15 is not accelerated quickly. As a consequence, the needle 11 is able to be bent by the base 17 and thereby contained within the container 10.

Figure 8:
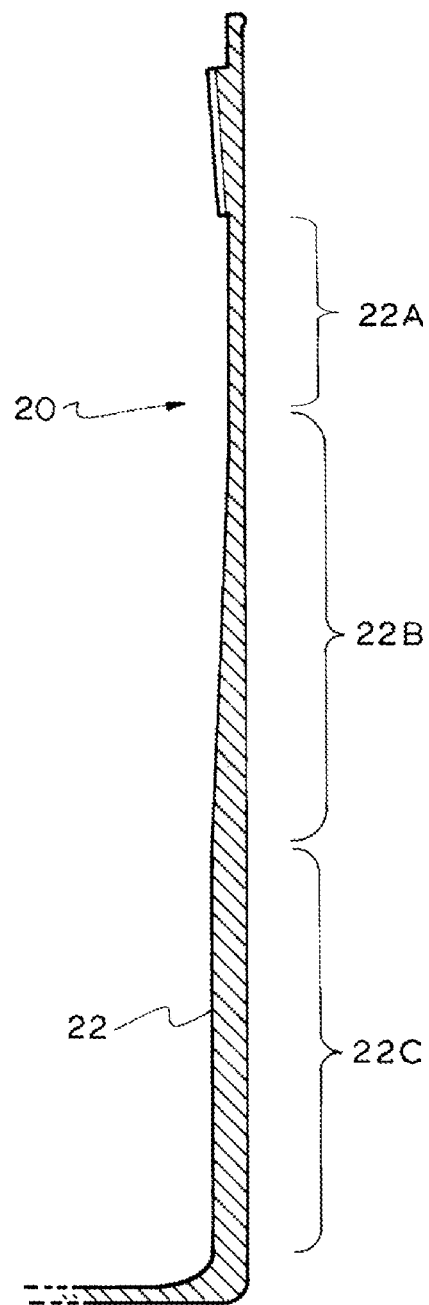
FIG. 8 is a view similar to FIG. 5 but in respect of the side wall of a container of a second embodiment.

In FIG. 8, a second embodiment of the present invention is illustrated in which a container 20 is provided with a side wall 22 which has three portions 22A, 22B, and 22C. The wall thickness of portions 22A and 22C are substantially constant preferably being 1.5 mm (0.059 inch) and 2.0 mm (0.079 inch) respectively. However, the intermediate portion 22B tapers so as to smoothly join portion 22A to portion 22C. Thus the side wall 22 may be said to taper intermittently, rather than continuously, as is the case with side 12 of FIG. 5. When subjected to the vertical crushing force indicated by arrows C in FIG. 2, container 20 concertinas at the portion 22A in the same manner as indicated in FIG. 7.

The foregoing describes only two embodiments of the present invention and modifications, obvious to those skilled in the plastic moulding arts, can be made thereto without departing from the scope of the present invention.

The term "comprising" (and its grammatical variations) as used herein is used in the inclusive sense of "including" or "having" and not in the exclusive sense of "consisting only of".

While the principles of the invention have been described above in connection with preferred embodiments, it is to be clearly understood that this description is made only by way of example and not as a limitation of the scope of the invention.

The invention claimed is:

1. A crush survival sharps container for a used syringe having an overall length and a needle with a needle tip, said container having a base, at least one side wall, a top, and a used syringe receiving aperture in said top closing said container and through which said used syringe can be passed, wherein a distance between said top and said base exceeds said overall length of said used syringe whereby said used syringe is wholly enclosed within said container when said used syringe is inserted into said container, each of said at least one side wall has a wall thickness which is greatest adjacent said base and thinnest adjacent said top, wherein a crushable portion of each of said at least one side wall adjacent said top concertinas when said container is subjected to a compressive crushing force in a direction generally from top-to-base, and wherein said base and a portion of each of said at least one side wall adjacent said base are sufficiently thick to prevent penetration thereof by a needle tip of a used syringe that has been inserted through said used syringe receiving aperture into said container and placed adjacent said base when said container is subjected to said compressive crushing force whereby said used syringe inserted through said aperture is retained within said container subjected to said compressive crushing force and said top, base and each said side wall of said container do not rupture.

2. The container as claimed in claim 1 wherein each of said at least one side wall tapers continuously in thickness from top to base.

3. The container as claimed in claim 1, wherein each of said at least one side wall tapers intermittently in thickness from top to base.

4. The container as claimed in claim 1, wherein said container has a transverse cross-sectional shape which is either generally circular or generally rectangular.

5. A method of providing a crush survival sharps container for a used syringe having an overall length and a needle with a needle tip, said container having a base, at least one side wall, a top, and a used syringe receiving aperture in said top closing said container and through which said used syringe can be passed, said method comprising:

provide each of said at least one side wall with a wall thickness which is greatest in a portion adjacent said base and thinnest in a portion adjacent said top; and providing said base, and the portion of each of said at least one side wall adjacent said base, with a sufficiently thickness to prevent penetration thereof by a substantially vertically aligned needle of a syringe placed adjacent thereto, when said container is subjected to a compressive crushing force in a direction generally from top-to-base, wherein said container is subjected to said compressive crushing force, said portion of each of said at least one side wall adjacent said top concertinas, said used syringe inserted through said aperture is retained within said container subjected to said compressive crushing force, and said top, base and each said side wall of said container do not rupture.

6. The method as claimed in claim 5, including the further step of: continuously tapering the thickness of each of said at least one side wall from top to base.

7. The method as claimed in claim 5, including the further step of: intermittently tapering the thickness of each of said at least one side wall from top to base.

8. The container as claimed in claim 3, wherein each of said at least one side wall has a top portion adjacent said top, a bottom portion adjacent said bottom, and an intermediate portion located between said top and bottom portions, wherein the top and bottom portions each has a substantially constant thickness and the intermediate portion has a tapered thickness between the top and bottom portions.

9. The method as claimed in claim 7, wherein intermittently tapering the thickness of each of said at least one side wall further comprises providing each of said at least one side wall with a top portion adjacent said top, a bottom portion adjacent said bottom, and an intermediate portion located between said top and bottom portions, wherein the top and bottom portions each has a substantially constant thickness and the intermediate portion has a tapered thickness between the top and bottom portions.

\* \* \* \* \*